United States Patent
Kodali (12)

(10) Patent No.: US 6,420,322 B1
(45) Date of Patent: *Jul. 16, 2002

(54) PROCESS FOR MODIFYING UNSATURATED TRIACYLGLYCEROL OILS: RESULTING PRODUCTS AND USES THEREOF

(75) Inventor: Dharma R. Kodali, Plymouth, MN (US)

(73) Assignee: Cargill, Incorporated, Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/841,484

(22) Filed: Apr. 22, 1997

(51) Int. Cl.$^7$ ............................................. C10M 101/04
(52) U.S. Cl. ....................... 508/452; 508/465; 554/165; 554/126
(58) Field of Search ............................... 508/452, 465; 554/126, 165

(56) References Cited

U.S. PATENT DOCUMENTS

| | | | |
|---|---|---|---|
| 2,361,018 A | * 10/1944 | Gerhart | 554/65 |
| 2,404,836 A | 7/1946 | Gerhart et al. | 260/42 |
| 2,443,044 A | 6/1948 | Lycan et al. | 260/407 |
| 4,100,120 A | 7/1978 | Maekawa et al. | 260/22 |
| 4,180,645 A | 12/1979 | Emmons et al. | 528/73 |
| 4,196,134 A | 4/1980 | Ball et al. | 260/404.8 |
| 4,783,274 A | * 11/1988 | Jokinen et al. | 508/376 |
| 5,229,023 A | 7/1993 | Landis | 252/57 |
| 5,288,805 A | 2/1994 | Kodali | 525/123 |
| 5,364,949 A | * 11/1994 | Neuss et al. | 554/161 |

FOREIGN PATENT DOCUMENTS

| | | |
|---|---|---|
| WO | WO91/14670 | 10/1991 |
| WO | WO 94/04579 | 3/1994 |

OTHER PUBLICATIONS

Carey, F., "10.12 The Diels–Alder Reaction", *Organic Chemistry*, Second Edition, p. 388 (1992).

Garrat, P.J., "Regiospecific Control in the Formation of Cyclohexenes from Dienes. The Catalysed and Non–catalysed Reactions of Butadiene and 2,3–Dimethylbutadiene with Methyl Sorbate," *J.C.S. Chem. Comm.*, p. 251 (1974).

Frank, et al. Food Technology, 36:6:71–76, "Automatic Determination of Oxidation Stability of Oil and Fatty Products", (Jun. 1982).

Laubli, et al. AOCS, 63:6:792–795, (Jun. 1986), "Determination of the Oxidative Stability of Fats and Oils: Comparison between the Active Oxygen Method (AOCS Cd 12–57) and the Rancimat Method".

A.O.C.S. Official Method Cd 12–57, Sampling and Analysis of Commercial Fats and Oils, "Fat Stability", pp. 1–4, (1989).

Kodali, et al. "Proceedings of the 1996 PORIM International Palm Oil Contrss—Competitiveness for the 21st Century, Chemistry and Technology," Plenary Lecture IV, pp. 465–474, (Sep. 1996).

* cited by examiner

*Primary Examiner*—Margaret Medley
(74) *Attorney, Agent, or Firm*—Merchant & Gould P.C.

(57) ABSTRACT

A process for modifying an unsaturated triacylglycerol oil, such as an vegetable oil stock, to enhance its fluidity and/or oxidative stability is provided. Lubricants containing a modified an unsaturated triacylglycerol oil and methods for their production and use are also provided.

35 Claims, No Drawings

PROCESS FOR MODIFYING UNSATURATED TRIACYLGLYCEROL OILS: RESULTING PRODUCTS AND USES THEREOF

BACKGROUND OF THE INVENTION

Vegetable oils are obtainable in large volumes from renewable resources and in general are characterized as readily biodegradable or "environmentally friendly". As a result, such oils and related materials are at least theoretically desirable for use in a wide variety of applications.

With respect to use for lubrication purposes, especially as machine lubricants, vegetable oils have not been fully desirable. Many vegetable oils do not possess the desired spectrum of characteristics relating to: viscosity index; pour point; oxidative stability; compatibility with additives; and, flash point/volatility among others.

Vegetable oils, such as a soybean oil ("SBO"), do however possess many desirable properties for use as a lubricant. In particular, SBO provides good boundary lubrication, good viscosity, high viscosity index and high flash point. In addition, SBO is nontoxic and readily biodegradable. For example, under standard test conditions (e.g., OCED 301D test method), SBO biodegrades up to 80% into carbon dioxide and water in 28 days, compared to 25% or less for typical petroleum-based lubricating fluids.

However, as exemplified by SBO, two characteristics, which are often major limitations for the utilization of vegetable oils as lubricants, relate to stability and low temperature behavior. In particular, vegetable oils such as SBO often contain substantial amounts of unsaturation (i.e., one or more carbon-carbon double bonds distributed along the fatty acyl chains). The sites of unsaturation may be associated with sufficient oxidative reactivity to render the oils insufficiently stable for use as lubricants. If efforts are made to reduce the unsaturation, for example by hydrogenation, generally undesirable changes in pour point and/or viscosity index result.

SUMMARY OF THE INVENTION

The present invention relates to unsaturated triacylglycerol oils, such as unsaturated vegetable oils. It particularly concerns modifications of selected vegetable oils to produce liquid products with preferred properties for use, for example as lubricant base stocks or in related uses. The unsaturated triacylglycerol oil is typically derived from plants, such as an oil seed, or an animal, such as tallow.

A process for modifying an unsaturated triacylglycerol oil, such as an unsaturated vegetable oil stock, to enhance its fluidity and/or oxidative stability is provided. The process includes (i) reacting the unsaturated triacylglycerol oil with an olefinic hydrocarbon to form a cycloaddition product and, optionally, (ii) at least partially hydrogenating the cycloaddition product to form a hydrogenated cycloaddition product. The cycloaddition product formed from the reaction with the olefinic hydrocarbon includes triacylglycerols which have at least one fatty acyl chain modified to include a cycloaddition adduct. If desired, either the cycloaddition product or the hydrogenated cycloaddition product may be fractionated using conventional techniques to alter the spectrum of modified and unmodifed triacylglycerols present. For example, the hydrogenated cycloaddition product may be fractionated to remove at least a portion of the saturated triacylglycerols, thereby enhancing the fluidity properties of the fractionated cycloaddition product with respect to the hydrogenated cycloaddition product.

Herein, when reference is made to the term "unsaturated triacylglycerol oil", the intent is to refer to a material comprising triacylglycerols, whether altered or not, derived from various plant and animal sources, such as oil seed sources. The term at least includes within its scope: (a) such materials which have not been altered after isolation; (b) materials which have been refined, bleached and/or deodorized after isolation; (c) materials obtained by a process which includes fractionation of an unsaturated triacylglycerol oil; and, also, (d) oils obtained from plant or animal sources and altered in some manner, for example through partial hydrogenation. It will be understood that the unsaturated triacylglycerol oil may include a mixture of triacylglycerols, and a mixture of triacylglycerol isomers. By the term "triacylglycerol isomers", reference is meant to triacylglycerols which, although including the same esterified acid residues, may vary with respect to the location of the residues in the triacylglycerol. For example, an unsaturated triacylglycerol oil such as a vegetable oil stock can include both symmetrical and unsymmetrical isomers of a triglyeride which includes two different fatty acyl chains (e.g., includes both stearate and oleate groups).

Herein, the result of adding an olefinic hydrocarbon to an unsaturated triacylglycerol oil, such as a vegetable oil stock, will be referenced as a "cycloaddition product." The term "cycloaddition product" includes within its scope practices which involve adding one or more olefinic hydrocarbons (e.g., dienic and/or monoolefinic hydrocarbons), on an average per molecule basis, to the unsaturated triacylglycerol oil. As used herein, the term "cycloaddition adduct" refers to an adduct produced by the reaction of an olefinic hydrocarbon and a double bond in a fatty acyl chain of a triacylglycerol. One example of a cycloaddition adduct is the adduct produced by a Diels-Alder reaction between a dienic hydrocarbon and a double bond in a triacylglycerol fatty acyl chain. Of course, it will be understood that the cycloaddition of the olefinic hydrocarbon will not necessarily be uniform in the mixture, but rather the result of the cycloaddition may be cycloaddition to some triacylglycerol molecules, and not to others. Nor will the cycloaddition product necessarily include the formation of at least one (on an average molecular basis) cycloaddition adduct per triacylglycerol molecule. For example, the cycloaddition product will typically include a number of unmodified triacylglycerols, i.e., triacylglycerols with fatty acyl chains lacking a cycloaddition adduct.

The cycloaddition adducts and hydrogenated cycloaddition adducts have an oxidative stability (as evidenced by their AOM value and/or active methylene content) which is increased with respect to the oxidative stability of the unsaturated triacylglycerol oil. The pour point of the hydrogenated cycloaddition adduct is generally less than the pour point of a product obtained from hydrogenation of the the unsaturated triacylglycerol oil by a corresponding amount. In some instances, the pour point of a hydrogenated cycloaddition adduct may even be reduced with respect to the pour point of the corresponding unsaturated triacylglycerol oil. The present method typically reduces the active methylene content of the unsaturated triacylglycerol oil at least about 10% and preferably by at least about 25% with respect to that of the corresponding unsaturated triacylglycerol oil.

The olefinic hydrocarbons used to form the cycloaddition product may include a diene and/or a monoolefinic hydrocarbon. The diene can react with a double bond ("dienophile") in a fatty acyl chain of a triacylglycerol molecule to form a 4+2 cycloadduct (Diels-Alder adduct). Similarly, monoolefinic hydrocarbons can act as a dienophile and react with triacylglycerol molecules having a fatty acyl chain which includes a diene moiety to form a 4+2 cycloadduct. Suitable monoolefinic compounds include cyclohexene, propene and butene. Alternatively, one of the double bonds of a diene such as cyclopentadiene or isoprene can act as a dienophile and react with a diene moiety within a fatty acyl chain of a triacylglycerol molecule. The diene moiety may exist naturally in the fatty acyl chain. More commonly, the double bonds of a polyunsaturated fatty acyl chain may be isomerized (e.g., by heating and/or by the addition of a catalyst such a iodine) to form a conjugated diene group within the chain. The olefinic hydrocarbons typically have a molecular weight of up to about 250 and preferably include no more than about 12 carbon atoms.

Lubricants including unsaturated triacylglycerols modified to have at least one fatty acyl chain including a cycloaddition adduct and processes of producing the lubricants are also provided herein. The process of producing the lubricant may also include blending the modified unsaturated triacylglycerols with one or more petroleum based lubricating fluids and/or other additives.

DETAILED DESCRIPTION

The present method may be utilized to increase the fluidity and/or enhance the oxidative stability of unsaturated triacylglycerol oils. For example, the method allows the production of vegetable oil based lubricants which, in addition to possessing very attractive lubricating properties, are extremely environmentally friendly. Since unsaturated triacylglycerol oil based lubricant base stocks are derived from natural materials, these lubricants have low toxicity and are readily biodegraded.

I. Properties of Unsaturated Triacylglycerol Oils.

A unsaturated triacylglycerol oil includes triacylglycerol molecules (sometimes termed triglycerides). In general, triacylglycerols comprise three long fatty acid chains esterified to glycerol; or, alternatively phrased, glycerol esterified by addition thereto of three long chain fatty acids. Herein, the terms "triacylglycerols" and "triglycerides" are intended to be interchangeable, and will in some instances be referred to by the abbreviation "TG".

Unlike petroleum-based lubricants, triacylglycerols have slight polarity on one end of the molecule due to the presence of the ester linkages. In some instances, this can be desirable when the material is used as a lubricating fluid, since the polar end of triacylglycerol molecules can become attracted to a metallic surface, while the nonpolar hydrocarbon region will generally project outwardly from metallic surfaces. This causes, in some instances, molecular attraction and alignment, and can result in better boundary lubrication with increased load carrying capacity and reduction in wear.

As indicated above, any given triacylglycerol molecule generally includes glycerol esterified with three fatty acid molecules. Thus, each triacylglycerol includes three fatty acid residues. In general, oils extracted from any given plant or animal source comprise a mixture of triacylglycerols, characteristic of the specific source. The mixture of fatty acids isolated from complete hydrolysis of the triacylglycerols in a specific source are generally referred to as a "fatty acid composition". By the term "fatty acid composition" reference is made to the identifiable fatty acid residues in the various triacylglycerols. The distribution of specific identifiable fatty acids is typically characterized by the amounts of the individual fatty acids as a weight percent of the total mixture of fatty acids obtained from hydrolysis of the particular oil stock.

For example, a typical fatty acid composition of soybean oil ("SBO") is as shown in Table I below.

TABLE I

Typical SBO Fatty Acid Composition

| Fatty acid | Weight Percent[1] |
| --- | --- |
| Palmitic acid | 10.5 |
| Stearic acid | 4.5 |
| Oleic acid | 23.0 |
| Linoleic acid | 53.0 |
| Linolenic acid | 7.5 |
| Other | 1.5 |

[1]Weight percent of total fatty acid mixture derived from hydrolysis of soybean oil.

Palmitic and stearic acids are saturated fatty acids and triacylglycerol acyl chains formed by the esterification of either of these acids do not contain any double carbon-carbon bonds. However, many fatty acids such as oleic acid, linoleic acid and linolenic acid are unsaturated. Oleic acid is an 18 carbon fatty acid with a single double bond; linoleic acid is an 18 carbon fatty acid with two double bonds or points of unsaturation; and linolenic is an 18 carbon fatty acid with three double bonds. More specifically, oleic acid is (Z)-9-octadecanoic acid;

linoleic acid is (Z,Z)-9,12-octadecadienoic acid;

linolenic acid is (Z,Z,Z)-9,12,15-octadecatrienoic acid; and

γ-linolenic acid is the (Z,Z,Z)-6,9,12 isomer of octadecatrienoic acid.

The average number of double bonds present per triacylglycerol molecule in an unsaturated triacylglycerol oil is referred to herein as the "average unsaturation content." The average unsaturation content of an unsaturated triacylglycerol oil may be calculated based from the distribution of fatty acids in the mixture produced by hydrolysis of the triacylglycerols. The distribution of fatty acids in a particular oil may be readily determined by methods known to those skilled in the art. Unsaturated triacylglycerol oils which are particularly suitable for use as starting materials in the present methods typically have an average unsaturation content of no more than about 5.0 and, preferably about 2.5 to about 3.5.

For example, on average, each triacylglycerol molecule in SBO contains about 4.5 double bonds, distributed among the various hydrocarbon chains (three chains in each triacylglycerol molecule), i.e., SBO has an average unsaturation content of about 4.5. This results from the fact that SBO includes a mixture of triacylglycerols and the triacylglycerol molecules of SBO generally each have a mixture of fatty acid residues.

Another measure of characterizing the average number of double bonds present in the triacylglycerol molecules of an unsaturated triacylglycerol oil is its Iodine Value. The Iodine Value of a triacylglycerol or mixture of triacylglycerols is determined by the Wijs method (A.O.C.S. Cd 1-25). The present method can be used to improve the fluidity and oxidative stability of unsaturated triacylglycerol oils having a wide range of Iodine Values. Typically, however, the present methods are employed with unsaturated triacylglycerol oils, such as vegetable oil stocks, having an Iodine Value of no more than about 150, for example, between about 50 to about 150, preferably about 70 to about 140, and, more preferably, about 80 to about 110.

For example, soybean oil typically has an Iodine Value of about 125 to about 135 and a pour point of about 0° C. to about −100° C. Hydrogenation of soybean oil to reduce its Iodine Value to about 90 or less can significantly improve its oxidative stability. Hydrogenated soybean oils with this level of Iodine Value, however, generally have substantially decreased fluidity as evidenced by an increase in pour point to about 10 to 20° C. or higher and can become solids at room temperature thereby limiting their use as a functional fluid.

During use and/or storage lubricants tend to break down due to oxidation or other degradation processes. When employed as a functional fluid, such as a lubricating fluid, a vegetable oil like soybean oil may oxidize during which polymerization and degradation occurs. Polymerization increases viscosity and reduces lubrication functionality. Degradation leads to breakdown products that may be volatile or corrosive. In either case, undesirable modifications to the lubricating characteristics of the fluid occur.

One measure of the oxidative stability of an unsaturated triacylglycerol oil is its "AOM value" (as determined by A.O.C.S. Method Cd 12-57) or Oil Stability Index (as determined by A.O.C.S. Cd 12b-92) converted to AOM hours. The AOM value is measured by passing a controlled flow of air through a heated sample of the oil. The generation of oxidation products typically includes an induction phase followed by a large increase in the rate of oxidation. The length of time (to the nearest hour) required for a sample of an oil to attain the specified peroxide value of A.O.C.S. Method Cd 12-57 is reported as the AOM value. The cycloaddition products and hydrogenated cycloaddition products produced by the present method preferably have an AOM value of at least about 50 hours and, more preferably, at least about 100 hours.

The conditions of lubricating fluid storage and/or use, which may involve exposure to substantial heat; pressure; metal surfaces, etc., can facilitate the oxidation process. It is desirable, then, to use lubricating fluids which are not readily susceptible to undesirable levels of oxidation, at least under normal storage and use conditions. Unsaturated fatty acyl chains are more readily susceptible to oxidation than saturated fatty acyl chains. Thus, triacylglycerols such as those found in soybean oils, which contain substantial amounts of oleic acid, linoleic acid and/or linolenic acid residues, can be subject to undesirable levels of oxidation.

The undesirable levels of oxidative instability are presently believed to be due in large part to the presence of polyunsaturated fatty acyl chains that contain "active methylene groups." As used herein, active methylene groups refers to —$CH_2$—groups which are situated between two double bonds in a fatty acyl chain, i.e., doubly allylic —$CH_2$—groups. When found, the active methylene groups are typically present in dienic and trienic polyunsaturated fatty acyl chairs. Active methylene groups are principally present in polyunsaturated fatty acid-containing triacylglycerol molecules, e.g., linoleic esters (with one active methylene group) and linolenic esters (with two active methylene groups). The term "active methylene content" as used herein refers to the average number of active methylene groups per triacylglycerol molecule in an unsaturated triacylglycerol oil. The active methylene content of an unsaturated triacylglycerol oil can be calculated based from the fatty acid composition of the unsaturated triacylglycerol oil.

It has been found that the oxidative stability, particularly as it relates to lubricating applications, of an unsaturated triacylglycerol oil is substantially enhanced if the Diels-Alder modified vegetable oil stock has an active methylene content of no more than about 1.5, preferably no more than about 1.0 and, more preferably, no more than about 0.5. For example, hydrogenation of a soybean oil/cyclopentadiene adduct to reduce its active methylene content to no more than about 1.0 can enhance the oxidative stability of the hydrogenated adduct with respect to the unhydrogenated adduct.

Of course, the propensity for a triacylglycerol to oxidize can also be reduced by hydrogenation of the double bond(s). That is, as the extent of hydrogenation increases (and the Iodine Value and active methylene content decrease), the propensity toward oxidation decreases. Unfortunately, however, hydrogenation generally is accompanied by concomitant, and undesirable, increase in "pour point", i.e., reduction in the fluidity of the oil. For example, a saturated monoacid triacylglycerol, tristearin (the stearic acid triester of glycerol; stearic acid is octadecanoic acid; $C_{18}H_{36}O_2$), has a melting point of 74° C., compared to triolein's 5° C. and trilinolein's −11° C.

It is apparent, then, that one cannot simply hydrogenate an unsaturated triacylglycerol oil such as soybean oil to obtain an oxidatively stable lubricating fluid. Thus, although soybean oil exhibits many properties desirable in a lubricating fluid, it has generally not been acceptable due to its propensity toward oxidation, and if hydrogenated, its undesirable levels of loss of fluidity (or increase of pour point).

In general, similar affects are observed with a variety of vegetable oils. For example, palm oil, which has a low average unsaturation content (e.g., an Iodine Value of about 50 to 60), is a semi-solid at room temperature and is generally not useful as a lubricant despite its relatively good oxidative stability. On the other hand, linseed oil, which has a very high level of polyunsaturation (fatty ester groups containing more then one double bond) and an Iodine Value of 170 to 180, has a high pour point due to the propensity of the polyunsaturated fatty acyl chains to crosslink and/or polymerize. Due to the propensity of linseed oil to crosslink or polymerize, unsaturated triacylglycerol oils used to produce a lubricant base stock by the present methods typically due not include a significant amount of linseed oil, e.g., less than about 25 wt. %, preferably no more than about 10 wt. %, and most preferably are substantially free (i.e., less than about 0.1 wt.&) of linseed oil.

Because of the tendency of unsaturated triacylglycerol oils having very high levels of polyunsaturation to polymerize, plant or animal derived oil stocks having an active methylene content of no more than about 3.0 and/or an Iodine Value of no more than about 150 are typically used to produce lubricant base stocks using the present method. Preferably, the unsaturated triacylglycerol oil has an active methylene content of no more than about 2.5, preferably no more than about 2.0 and/or includes no more than about 15 wt. % (on a fatty acid composition basis), preferably no more than about 10 wt. % of trienic (i.e., having three double bonds) unsaturated fatty ester groups, such as esters of linolenic acid.

II. Modifications to Unsaturated Triacylglycerol Oils for Use as Lubricating Fluids A. General The fluidity of a material is in part determined by the ability of molecular packing, intermolecular interactions, and molecular weight. In general, increasing branching of a hydrocarbon, especially towards the methyl end, or introducing unsaturation in the chain (cis typically produces a greater effect than trans), increases fluidity since it disrupts packing. By "increase in fluidity" in this context, reference is meant to reduction in "pour point" or "melting point". The term "pour point" as used herein refers to the temperature at which the material stops flowing (as measured by ASTM method D 97). Thus pour point is a property which may involve a phase change but generally is based on a change in the viscosity properties of the material. The term "melting point" as used herein refers to the temperature at which a material transforms from a solid to a liquid, i.e., when a phase change involving a heat of fusion occurs.

In addition to pour point, the viscosity of an unsaturated triacylglycerol oil or modified version thereof at room temperature or an elevated temperature (e.g., 40° C.) may be used to characterize its fluidity. Unless otherwise indicated, viscosities reported herein are in centipoise (cP) as determined using a Brookfield viscometer type R.V.F. at a 20 rpm setting. The present cycloaddition products and hydrogenated cycloaddition products typically have a viscosity at 40° C. of no more than about 200 cP and, preferably, no more than about 100 cP.

For some lubricants, the desired fluidity properties may be specified in terms of a viscosity index (as determined by ASTM method D 2270). It is characteristic of triglyceride oils that their viscosity fluctuations as a function of temperature change to a lesser extent than the viscosities of petroleum based mineral oils. The viscosity-to-temperature properties of each oil can be characterized in terms of the viscosity index ("VI"). A higher viscosity index signifies that the viscosity of the oil concerned changes less as a function of changes in temperature. The viscosity indexes of triglycerides (typically in the range of about 180 to about 275) are clearly higher than those of petroleum based mineral oils with no additives (typically 50–120), so that triglycerides are to their nature so-called multigrade oils. This is a considerable importance under conditions in which the operating temperature may vary within rather wide limits. The modified unsaturated triacylglycerol oils produced by the present methods generally have a viscosity index which is quite similar to the original triacylglycerol oil. Preferably, the present modified unsaturated triacylglycerol oils have a viscosity index of at least about 150 and, more preferably, at least about 175. This is typically achieved by selecting a starting unsaturated triacylglycerol oil which has close to the viscosity index desired for the modified product.

As part of the development of the present techniques, it was theorized that triacylglycerols having therein substantial sites of unsaturation could be improved, with respect to fluidity, by generation of "spacer groups" or moieties extending from at least some of the long acyl chains. It was foreseen that such "spacer groups" would limit the ability for the fatty acyl chains to pack closely. At the same time, a spacer group generated via a Diels-Alder reaction would move a double bond from the acyl chain backbone to a remote position (i.e., into a portion of a ring extending from the acyl chain backbone). This can create at least two benefits: (i) a decrease in the possibility of double bond migration to generate a less stable polyunsaturated chain, e.g., through the formation of a conjugated diene or triene fatty acyl chain; and (ii) the bicyclic nature of the adduct results in the oxidation products of the remote double bond being non-volatile. Thus, it was theorized that if, after spacer group introduction, the triacylglycerols were partially or fully hydrogenated, a desirable lubricating fluid could result which would possess appropriate characteristics with respect to both stability towards oxidation and, desirably, low pour point or melting point.

B. Cycloaddition Adducts

Modification of unsaturated triacylglycerol oils through formation of a cycloaddition product and, optionally, subsequent hydrogenation of the cycloaddition product can increase the oxidative stability with respect to the unmodified vegetable oil stock, e.g., increase the AOM value by at least about 50%. Preferably, the formation of a cycloaddition product and/or the subsequent hydrogenation reaction can be used to increase the AOM value of an unsaturated triacylglycerol oil by a factor of at least about 2 (i.e., increased by at least about 100%) with respect to the unmodified unsaturated triacylglycerol oil.

It has been found that cycloaddition reactions may be used to modify unsaturated triacylglycerol oils to improve their properties as lubricating fluids. It can be theorized that when an olefinic hydrocarbon, such as a diene, is reacted with vegetable oil having an unsaturation therein, a carbon-carbon double bond or point of unsaturation in the unsaturated triacylglycerol oil can act as a dienophile and cycloadd to the conjugated diene by means of a [4+2] cycloaddition, or Diels-Alder reaction.

Cyclopentadiene is a well-known active diene, for the conduct of [4+2] cycloadditions. Indeed, cyclopentadiene will add to itself, in a dimerization, via a [4+2] cycloaddition, to form, as a Diels-Alder adduct, dicyclopentadiene. This is a reversible reaction which can be used to generate cyclopentadiene in situ, upon application of heat to dicyclopentadiene. For example, two molecules of cyclopentadiene can be reversibly generated from dicyclopentadiene at temperatures above about 170° C. In one embodiment of the invention, a vegetable oil stock such as SBO is heated at about 200 to about 300° C. in the presence of dicyclopentadiene. Under such conditions, rather than reacting with another cyclopentadiene molecule to reform dicyclopentadiene, a cyclopentadiene molecule can react with a fatty ester double bond to form a triacylglycerol/cyclopentadiene cycloadduct. This typically occurs when the concentration of cyclopentadiene present at any one time during the reaction are relatively low. Under such conditions, the cyclopentadiene may be relatively efficiently trapped by reaction with a double bond in a triacylglycerol fatty acyl chain before the cyclopentadiene has an opportunity to react with a second molecule of cyclopentadiene.

Cyclopentadiene, it has been found, readily adds to points of unsaturation in vegetable oils. In Scheme 1, an example is provided. Of course, reactions with substituted cyclopentadienes (e.g., alkyl substituted cyclopentadienes such as 1-methylcyclopentadiene and 2-methylcyclopentadiene) are also feasible, as illustrated in Scheme 1.

Scheme 1

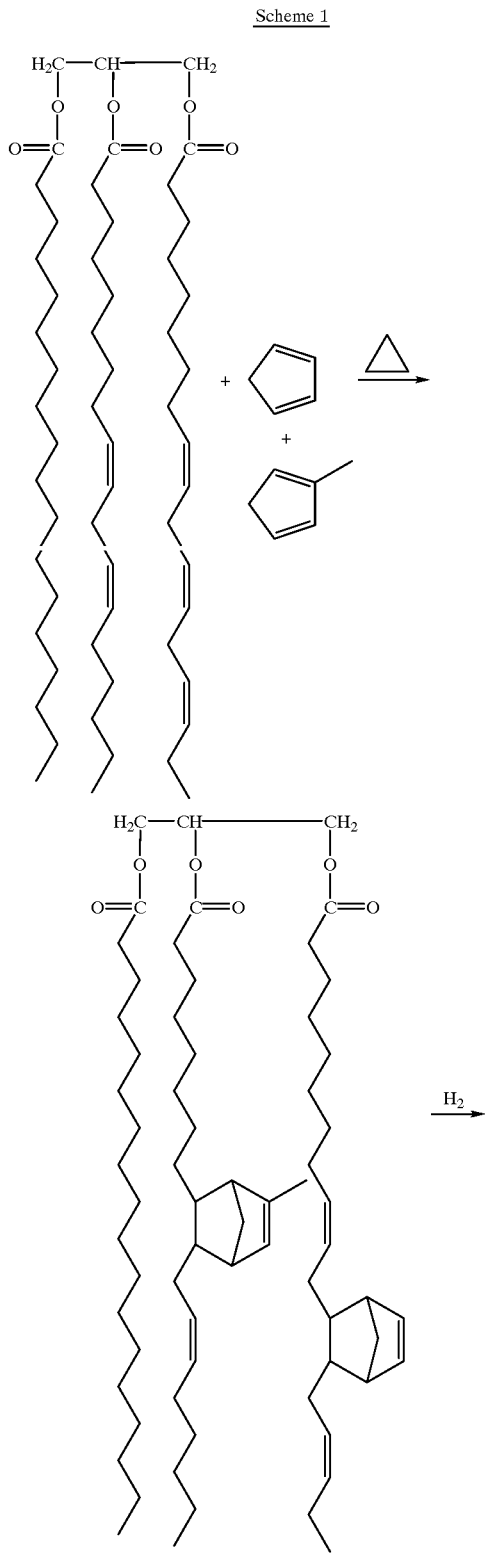

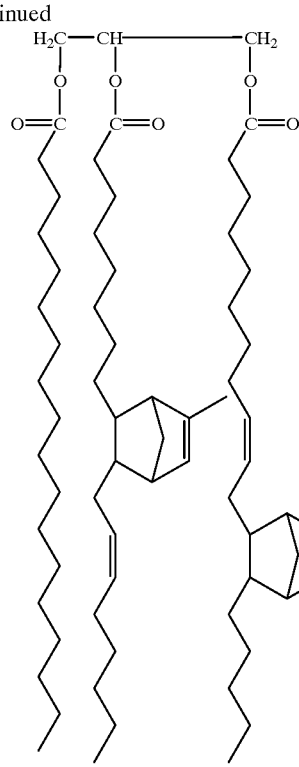

As illustrated in Scheme 1, a diene such as cyclopentadiene or 2-methylcyclopentadiene can with a double bond in one of the fatty acyl chains of a triacylglycerol. The reaction may occur at with a double bond in either a fatty acyl chain esterified at a primary hydroxyl group of the glycerol (e.g., the cyclopentadiene adduct shown in Scheme 1) or in a fatty acyl chain chain esterified at a secondary hydroxyl group of the glycerol (e.g., the 2-methylcyclopentadiene adduct shown in Scheme 1). The formation of a cycloadducts does not alter the Iodine Value or average unsaturation content of an unsaturated triacylglycerol oil, i.e., the number of double bonds present per triacylglycerol molecule may remain unchanged. The number of active methylene groups present can, however, be reduced by cycloaddition of an olefinic hydrocarbon to a polyunsaturated fatty acyl chain. For example, the reaction of cyclopentadiene with the C12-double bond of a linolenic ester chain as shown in Scheme 1, destroys the allylic character of two methylene groups (at both the 11 and 14 positions). The new double bond present in the bicyclic ring moiety also provides a potential oxidation site, but the resulting oxidation product maintains the integrity of the molecule. Moreover, as discussed herein, it is believed that the introduction of bulky bicyclic rings onto acyl chains of triacylglycerols leads to a cycloaddition product having a low viscosity.

As illustrated in Scheme 1, there are a variety of cycloadducts that can be formed from the reaction of a single diene with a unsaturated triacylglycerol oil. It is expected that reaction between the diene and an unsaturated triacyglycerol could occur at one or more of a number of positions along a fatty acyl chain. The reaction may also occur with double bonds on one or more of the fatty acyl chains within a triacylglycerol molecule.

If a further improvement in the oxidative stability of a cycloaddition product is desired, it is generally not necessary to exhaustively hydrogenate the cycloaddition product. Typically, hydrogenation of the cycloaddition product sufficiently to reduce the active methylene content by at least about 10% will produce an observable improvement in oxidative stability. Preferably, the cycloaddition product is hydrogenated to a sufficient degree to decrease the active methylene content by at least about 0.25 and, preferably, to decrease the active methylene content to a value of no more than about 0.5. Most preferably, the hydrogentation is carried out to a sufficient amount to substantially eliminate all of the allylic methylene groups (i.e., to reduce the active methylene content of the cycloaddition product to no more than about 0.1). In the process of eliminating the allylic methylene postions, an even larger number of isolated double bonds are also typically eliminated. Stated otherwise, the hydrogenation reaction will typically reduce the average unsaturation content of the cycloaddition product by an even larger amount than the observed reduction in active methylene content. The introduction of the bulky bicyclic moieties allows the hydrogenatation reaction to be carried out to a much greater extent without the substantial losses in viscosity properties that would be expected upon hydrogenation of the original unsaturated triacyglycerol oil.

The cycloaddition reaction to produce a cycloaddition product can be carried out in a number of ways as illustrated by the following discussion of the production of a SBO/cyclopentadiene product. The SBO/cyclopentadiene adduct may be produced by a variety of methods which at least include (i) adding dicyclopentadiene to the SBO, (ii) simultaneously mixing the ingredients into a reaction vessel or (iii) separately cracking dicyclopentadiene to generate cyclopentadiene and then adding the cyclopentadiene to a reaction vessel containing the SBO. By way of example, the SBO/dicyclopentadiene adduct may be made by charging the SBO into a closed reactor purged with an inert gas such as nitrogen. The SBO is heated to about 260° C. with constant stirring which is continued throughout the reaction with dicyclopentadiene. Dicyclopentadiene is typically added at a steady rate under the surface of the heated SBO in the reactor. While not intending to be bound by any theory, it is believed that as the dicyclopentadiene enters the vessel the dicyclopentadiene dedimerizes into two molecules of cyclopentadiene and which then reacts with the SBO double bonds. After the addition of the dicyclopentadiene is completed, heating of the reaction mixture is generally continued at a temperature of not more than 300° C., and preferably not more than about 275° C. for about 0.25 hour to about 5 hours. The reaction is generally permitted to proceed until substantially all of the cyclopentadiene has reacted with the SBO to form cycloadducts. Thereafter the copolymer reaction product is cooled and removed from the reaction vessel. Optionally, the volatile components left in the reaction vessel may be removed by applying a vacuum (e.g., less than about 50 mm Hg) during about the last 30 minutes to about the last hour of the reaction.

The cycloaddition reaction, it is believed, has at least two beneficial affects. First, it helps to reduce the susceptability of the unsaturated triacylglycerol oil to oxidation. A manner in which this occurs, is that the presence of active methylene groups, for example, the number of doubly allylic hydrogens (positioned in methylene groups bonded to two vinyl groups), is reduced. In addition, the presence of the resulting cycloaddition moiety in the fatty acyl chains appears to decrease the ease of packing and thus helps to maintain a low pour point or melting point, even after significant levels of hydrogenation.

It is important to recognize that in commercial practice of the techniques described herein, the techniques will typically be operated on mixtures of triacylglycerols either isolated as a plant or animal oil, e.g., by various oil seeds processing techniques, or resulting from alteration of such oils, for example by prior partial hydrogenation.

Herein, when it is said that the "unsaturated triacylglycerol oil" contains an average of at least one double bond per triacylglycerol (or triacylglycerol) molecule therein ("unsaturation content"), reference is meant to the average double bond presence in the triacylglycerol mixture, on a per triacylglycerol molecule basis. Unmodified SBO, as indicated above, generally contains an average of about 4.5 double bonds per molecule. Examples of other unmodified vegetable oils and fish oils include those listed in Table II below (together with typical Iodine Values for the oils). Of course, the "unsaturated triacylglycerol oil" is employed in applications according to the present invention may comprise a mixture of oils from a variety of sources.

TABLE II

| Unsaturated Triacylglycerol Oil | Iodine Value |
| --- | --- |
| Rapeseed oil | 97–108 |
| Corn oil | 103–128 |
| Peanut oil | 84–100 |
| Safflower oil | 140–150 |
| Olive oil | 80–88 |
| Sunflower oil | 125–136 |
| Cottonseed oil | 99–113 |
| Menhaden oil | 150–160 |
| Herring oil | 115–160 |

When it is intended that the triacylglycerol is to act as the diene component in the cycloaddition reaction, the starting unsaturated triacylglycerol oil may be subjected to an isomerization reaction to convert the polyunsaturated fatty acyl chains into conjugated isomers. A conjugation catalyst, such as ruthenium, rhodium, nickel or compounds thereof, sulfur dioxide, iodine or a compound capable of generating iodine, may employed in the this process. Compounds capable or generating iodine include, for example, hydriodic acid, iodine mono-chloride, iodine trichloride and iodine mono-bromide. When sulfur dioxide is the catalyst, it is typically added as the free compound. When nickel is the catalyst, it is typically used as an activated nickel on carbon catalyst.

In carrying out this isomerization reaction, the unsaturated triacylglycerol oil is typically heated with the catalyst at a temperature of about 200° C. to 270° C. in the presence of about 0.001% to 1.5% by weight (based on unsaturated triacylglycerol oil) of the catalyst. With soybean oil, conjugation times of 20–30 minutes typically produce about 35% conjugated linoleic acids.

Herein, in connection with hydrogenation of the cycloaddition product, reference will in some instances be made to "at least partially hydrogenating". By this, it is meant that the mixture including cycloaddition adduct and any unreacted (via cycloaddition) triacylglycerol is treated under appropriate conditions to reduce at least some of the double bonds present by addition of hydrogen thereacross. In order to be considered "at least partially hydrogenated" as the term is used herein, there should be a reduction of at least 10%, and preferably at least about 25% of the total number of double bonds (on an average per molecule basis for the whole cycloaddition product). The term "on an average per molecule basis" in this connection, is meant to refer to on an average per total of triacylglycerol molecules in the reaction mixture, whether those molecules includes a cycloaddition adduct or are an unreacted triacylglycerol molecule.

From the above, it will be understood that the intent is to reference techniques that may be practiced on mixtures, without precise analysis of exact adduct and unreacted triacylglycerol presence in the mixture, but rather with a general understanding of overall diene take-up and, optionally, hydrogen take-up, during modification. The intent, in general, is to obtain a stock of desirable property with respect to, inter alia, pour point and stability. In some instances, this may involve partially hydrogenating a mixture of: unsaturated triacylglycerol oil which has previously been treated with diene; and, unsaturated triacylglycerol oil which has not been previously treated with diene. In other instances, it may comprise partially hydrogenating a mixture of more than one unsaturated triacylglycerol oil which has been differently treated with diene; or, unsaturated triacylglycerol oils from different sources which have been similarly treated with diene; etc. Indeed, it is foreseen that in some applications blends may well be desirable, depending on the use to which the lubricating stock is to be placed. The present method is particularly useful for producing lubricant base stocks which include a predominant amount of a modified unsaturated triacylglycerol oil, e.g., a lubricant base stock including at least about 50 wt. % and, preferably, at least about 75 wt. % of the modified unsaturated triacylglycerol oil. By employing the present method, biodegradable, unsaturated triacylglycerol oil-based base stocks which have a combination of oxidative stability and viscosity properties suitable for a variety of lubricant applications. Preferred embodiments of the invention include such base stocks having an oxidative stability characterized by an AOM value of at least about 50 hours, preferably at least about 100 hours, and/or an active methylene content of no more than about 1.5 and, preferably, no more than about 1.0. Such preferred base stocks typically have fluidity properties characterized by a viscosity index of at least about 150 and a viscosity at 40° C. of no more than about 200 cP and, preferably, no more than about 100 cP.

1. Some Preferred Vegetable Oils.

Techniques according to the present invention, as will be understood from the experimental report below, were particularly developed for generation of desirable lubricating fluids from soybean oils. In general, this is because of the particular level of unsaturation found in soybean oils, as well as the physical properties both of starting materials and the final adducts. In general, improvement is observed if the extent of cycloaddition is at least 0.5 diene molecules added per soybean oil triacylglycerol molecule, on average. Generally, reactions to the extent of 0.7 to 1.5 dienes added, per soybean oil triacylglycerol molecule, will be preferred. This can readily be controlled by judicious choice of the starting vegetable oil stock, the type and amount of olefinic hydrocarbon employed and the reaction conditions. More broadly, improvement in the oxidative stability of an unsaturated triacylglycerol oil, such as a vegetable oil stock, can be produced through the cycloaddition of at least about 0.25 olefinic hydrocarbon molecules on average per triacylglycerol molecule. It has been found that the cycloaddition up to about 2.0 olefinic hydrocarbon molecules on average per triacylglycerol molecule can generally produce a substantial enhancement in the oxidative stability of the unsaturated triacylglycerol oil.

Other vegetable oils which, it is foreseen, may be modified with techniques according to the present invention, include: rapeseed oil, olive oil, sunflower oil, safflower oil, peanut oil, cottonseed oil, crambe oil, mustard oil, and meadowfarm oil. As used herein, "rapeseed oil" includes high erucic acid rapeseed oil ("HEAR") and low erucic acid rapeseed oil ("LEAR" or canola oil). Variants of some of the other oils listed above are also known, e.g., high oleic and very high oleic sunflower and canola oils. As discussed herein, these vegetable oils may be employed in the present invention as isolated or in altered form, as well as with oil from a single source or mixtures of one or more of the types of oils (or altered forms thereof).

2. Some Preferred Dienes; Conduct of the Preferred Cycloaddition.

At the present time, it is foreseen that cyclopentadiene and 1-alkyl cyclopentadiene or 2-alkyl cyclopentadienes (for example, 1-methyl or 2-methyl cyclopentadienes or mixtures thereof) will 4 be preferred. Such materials are readily obtainable, easily handled, and result in the introduction of only hydrophobic (alkyl) substitution in the soybean oil chains. In addition, cyclopentadienes are relatively active dienes in cycloaddition reactions, are relatively easy to control and can be generated in situ from the "cracking" of the corresponding dicyclopentadiene. Other dienes which can be used to modify a unsaturated triacylglycerol oil according to the present invention include cyclohexadiene and acyclic dienes such as isoprene and dimethylbutadiene. The olefinic hydrocarbon preferably includes cyclopentadiene and/or an alkyl substituted cyclopentadiene (e.g., cyclopentadiene substituted with a C1–C4 alkyl group). In general, when the cycloaddition reaction involves the use of cyclopentadiene, the following conditions will be preferred: reaction of a sufficient amount of cyclopentadiene to increase the AOM value of the unsaturated triacylglycerol oil by at least about 10% (e.g., a sufficient amount to form on average about 0.25 to about 2.0 cycloadducts per triacylglycerol molecule); reaction at a temperature of at least about 200° C.; and reaction for a sufficient time to achieve the desired increase in oxidative stability and/or fluidity; and removal of unreacted olefinic hydrocarbon at the end of the reaction (e.g., by stripping the reaction product under vacuum).

3. Hydrogenation.

The cycloaddition adducts, such as a SBO/cyclopentadiene adduct, can be readily reduced using various techniques, for example by hydrogenating the adduct with hydrogen in the presence of a heterogeneous noble or transition metal hydrogenation catalyst (e.g., a paladium, platinum, nickel, or highly selective copper-chromium catalyst). Methods and conditions suitable for hydrogenating the cycloaddition adducts include those typically employed to hydrogenate vegetable oil stocks, such as soybean oil. One example of a catalyst suitable for use in hydrogenating the present cycloaddition adducts, is a nickel catalyst deposited on the surface of an inert support (e.g., a nickel-carbon catalyst such as Nysel®, available from Engelhard). The degree of hydrogenation can be selected by controlling conditions and monitoring the hydrogenation reaction as it proceeds. In general, hydrogenation will be conducted until stability of the resulting oil, with respect to oxidation, has been increased to a desired level. For example, the hydrogenation of the cycloaddition adduct is typically allowed to continue until the Iodine Value has been decreased to no more than about 110, preferably no more than about 90 and/or the active methylene content has been reduced to no more than about 1.5, preferably no more than about 1.0 and, more preferably, no more than about 0.5.

III. Some Preferred Products

A. A Lubricating Fluid Base.

Techniques according to the present invention can be utilized to prepare preferred lubricating fluid bases, or base stocks, from various plant or animal oils. As indicated above, a soybean oil derivative can be prepared, for example, as a lubricating base stock. Lubricating base stocks would, in general, be fluids that can be used as the ingredient present in the highest amount by weight in a wide variety of lubricating fluids, for example, as the base fluid stock for crankcase oils, transmission oils, power transfer fluids (e.g., hydraulic fluids), gear oils and greases. It is foreseen that such materials may be used as the lubricating fluid base in such industries as: the automotive industry, metalworking and metal forming industries, earth moving industry, and general manufacturing.

B. Preparation of Lubricating Fluids from the Base Stock.

The major constituent of a lubrication fluid is a base oil (base stock) formulated with small amounts of additives. The base oil provides the primary lubricant functionality and performance. The additives enhance the performance of the base oil and also provide additional advantages and/or remove the shortcomings of the base oil.

Once base stocks according to the present invention are developed, they can be readily converted into lubricating fluid by the provision therein of appropriate additives. For example, to make lubricants, such as motor oils, transmission fluids, gear oils, industrial lubrication oils, metal working oils, and the like, one typically starts with a lubricant grade of the present cycloaddition adduct or hydrogenated cycloaddition adduct (referred to collectively herein as a "cycloaddition adduct base stock"). Into this "base stock" is typically blended a small amount of specialty chemicals that enhance lubricity, inhibit wear and corrosion of metals, and retard damage to the fluid from heat and oxidation.

Anti-wear agents, extreme pressure agents and friction modifiers have been developed that are generally organic or organometallic compounds containing halogens, sulfur, phosphorus, or a combination of the three. Halogens have noted low-temperature metal-coating activity but can cause serious corrosion problems at the higher operating temperatures of motor vehicles or industrial machinery and have environmental problems upon disposal. Manufacturers have, therefore, more recently switched to the use of derivatives of sulfur and phosphorus for lubricant additives in place of halogen-containing additives.

The amount and type of additives required in a formulation depends upon the severity of the application; usually the additives vary from 5 to 20% of the total formulation. Types of additives that commonly used in lubricant formulations include: viscosity index improvers (e.g., a few % polyisobutylenes and/or polymethacrylates); oxidation inhibitors (e.g., 0.5–1.0% di-tert-butyl-p-cresol and/or other phenolic antioxidant); pour point depressants (e.g., circa 1% of a polymethacrylate); antiwear agents (e.g., a few % of a polar fatty acid compound and/or a zincdiorganodithiophosphate); detergent dispersants (e.g., 2–20% of a sulfonate and/or a phosphate); and rust inhibitors (e.g., circa 1s of a mildly polar organic acids, organic phosphates and/or amines).

IV. Illustrative Experimental Examples

Example 1
Soybean Oil/Cyclopentadiene Adduct

A steel par reactor was charged with 394g of soybean oil. After closing and purging the reactor with nitrogen, the reactor was heated to 260° C. The contents of the reactor were stirred throughout the heating reaction and cool down periods. Dicyclopentadiene (30g) was added to the hot soybean oil over the period of 1 hour. The reaction was maintained at 260° C. for an additional 23 minutes after the addition of the dicyclopentadiene had been completed. The pressure in the reactor was then released to a cold trap and the vessel was connected to a pump to strip the volatile components from the vessel. The stripping was continued for 10 minutes during which 13.2g of material were removed from the reactor. After stripping, the reaction product was cooled to room temperature. The modified soybean oil product had a pour point of −12° C. and a viscosity of 55 cP at 39.5° C. (Brookfield Viscometer). The starting soybean oil had a pour point of −70° C. and a viscosity of about 30 cP at 40° C.

Example 2
Hydrogenated Soybean Oil/Cyclopentadiene Adduct

The modified soybean oil product prepared in Example 1 was placed in a steel parr reactor together with 3.23 g of a Nysel® 545 nickel catalyst (available from Engelhard). The reactor was purged under vacuum and then maintained under an atmosphere of 25 psi hydrogen for a period of 3.0 hours. Sample aliquots were removed for pour point and Iodine Value analysis at 15 minute, 1 hour, 1.5 hour and 2.5 hour intervals after initiation of the reaction. The results of these analysis are shown in Table III below. The final product was a semi-solid at room temperature and had a viscosity of 75 cP at 40° C. (Brookfield Viscometer).

TABLE III

| Time (hr) | Iodine Value | Pour Point (° C.) |
| --- | --- | --- |
| 0.25 | 122 | −9 |
| 1 | 76.3 | −5 |
| 1.5 | 75.0 | 0 |
| 3.0 | 72.7 | 11 |

Example 3
Soybean Oil—Cyclopentadiene Adduct Ii

Soybean oil (367.5 g) and dicyclopentadiene (55.5 g) were reacted using the procedure described in Example 1 above. The cyclopentadiene was added to the soybean oil at 260° C. over a period of 1 hour. The reaction mixture was heated at 260° C. for an additional 40 minutes after addition of the dicyclopentadiene. The mixture was then stripped under vacuum for 10 minutes to yield 413 g of a modified soybean oil product having a pour point of —4.5° C. and a viscosity of 70 cP at 40° C. (Brookfield Viscometer).

Example 4
Hydrogenated Soybean Oil/Cyclopentadienes Adduct II

The soybean oil/cyclopentadiene adduct produced in Example 3 above (286.6 g) was hydrogenated in the presence of 2.86 g of a nickel catalyst using the procedure described in Example 2. Aliquots of the reaction mixture were removed at 0.5, 1.0, 1.5 and 2.0 hours for pour point and Iodine Value analysis. The reaction was stopped after 2.5 hours. Each of the 5 gram aliquots were mixed with 100 mg of diatomaceous earth and 1 drop of citric acid and filtered at 450° C. prior to analysis. The results of the analysis are shown in Table IV below. The final product had a viscosity of 82.5 cP at 40° C. (Brookfield Viscometer).

TABLE IV

| Time (hr) | Iodine Value | Pour Point (° C.) |
| --- | --- | --- |
| 0.5 | 126.2 | −0.5 |
| 1.5 | 84.2 | 4 |
| 2.0 | 49.7 | na |
| 2.5 | 21.7 | 10.5 |

Example 5
Tallow/Cyclopentadienes Adduct

Tallow (395.25 g) and dicyclopentadiene (38.25 g) were reacted using the procedure described in Example 1 above.

The dicyclopentadiene was introduced to the hot tallow over a period of 64 minutes and the reaction mixture was maintained at 260° C. for an additional 36 minutes after the addition of the dicyclopentadiene had been completed. The reaction mixture was cooled and stripped for 10 minutes during which time 5.4 g of distillate was removed. The resulting tallow/cyclopentadiene adduct had a pour point of 25° C. and a viscosity of 67.5 cP at 40° C. (Brookfield Viscometer).

Example 6
Hydrogenated Tallow/Cyclopentadienes Adduct

The tallow/cyclopentadienes adduct of Example 5 (343.5 g) was hydrogenated in the presence of 3.46 g of a nickel catalyst for 3 hours. The final product had a pour point of 35° C. and an Iodine Value of 58.2.

Example 7
Tallow/Cyclopentadienes Adduct II

Tallow (372 g) and dicyclopentadiene (29 ml) were reacted according to the procedure described in Example 1 above. The dicyclopentadiene was added to the tallow at 260° C. over a period of 62 minutes. Stripping of the reaction product under vacuum for a period of 10 minutes resulted in a removal of 8.9 g of distillate. The final product had a viscosity of 65 cP at 40° C.

Example 8
Soybean Oil/Isoprene Adduct

Soybean oil (381.3 g) and isoprene (28.7 g) were reacted using a modification of the procedure described in Example 1 above. The isoprene was mixed with the soybean oil prior to introduction of the starting material into the reactor. After sealing and purging the reactor with nitrogen, the reaction mixture was heated to 260° C. for a period of 2 hours. Stripping of the reaction mixture resulted in removal of 12 g of distillate. The resulting soybean oil/isoprene adduct had a pour point of −12° C. and an Iodine Value of 139.9.

Example 9
Hydrogenated Soybean Oil/Isoprene Adduct

The soybean oil/isoprene adduct of Example 8 was hydrogenated according to procedure described in Example 2 above. The adduct (374 g) was hydrogenated in the presence of 3.74 g of a nickel/carbon catalyst for a period of 2.5 hours. Aliquots were removed at half hour intervals for pour point analysis. The results are shown in Table V below.

TABLE V

| Time (hr) | Pour Point (° C.) |
|---|---|
| 0.5 | 10.5 |
| 1.0 | 27 |
| 1.5 | 33 |
| 2.0 | 39 |
| 2.5 | 45 |

Example 10
Soybean Oil/Isoprene Adduct

A mixture containing 75 wt. % soybean oil and 25 wt. % isoprene was reacted by heating for 120 minutes at 260° C. according to the procedure described in Example 8 above. The reaction mixture was stripped under vacuum for 25 minutes. The resulting soybean oil/isoprene adduct had a pour point of −12° C.

Example 11
Soybean Oil/Dimethylbutadiene Adduct

A mixture containing 92 wt. % soybean oil and 8 wt. % 2,3-dimethylbutadiene were reacted by heating for 110 minutes at 260° C. according to the procedure described in Example 8 above. The reaction product was stripped under vacuum for 10 minutes during which time 2.5 g of distillate were removed.

Example 12
Hydrogenated Soybean Oil/Dimethylbutadiene Adduct

The soybean oil/dimethylbutadiene adduct prepared in Example 11 (354 g) was hydrogenated in the presence of 3.5 g of a nickel/carbon catalyst for a period of 1.5 hours. Aliquots of the reaction mixture were removed at half hour intervals and analyzed for pour point. The results of the analysis are shown in Table VI below.

TABLE VI

| Time (hr) | Pour Point (° C.) |
|---|---|
| 0.5 | 24 |
| 1.0 | 39 |
| 1.5 | 43.5 |

TABLE VII

| Adduct of Example | Adduct* | Reactant Ratio | Pour Point (° C.) | Iodine Value | Viscosity @ 40° C. (cP) |
|---|---|---|---|---|---|
| 1 | SBO/CPD | 93/7 | −12 | 127 | 55 |
| 2 | SBO/CPD[H] | 93/7 | 14–15 | 72.7 | 75 |
| 3 | SBO/CPD | 87/13 | −3–−6 | — | 70 |
| 4 | SBO/CPD[H] | 87/13 | 10–11 | 21.7 | 82.5 |
| 5 | TALLOW/CPD | 91/9 | 25 | — | 67.5 |
| 6 | TALLOW/CPD[H] | 91/9 | 35 | 58.2 | — |
| 7 | TALLOW/CPD | 93/7 | — | — | 65 |
| 8 | SBO/ISP | 93/7 | −12 | 140 | — |
| 9 | SBO/ISP[H] | 93/7 | 45 | — | — |
| 10 | SBO/ISP | 75/25 | −12 | — | — |
| 11 | SBO/DMBD | 92/8 | — | — | — |
| 12 | SBO/DMBD[H] | 92/8 | 42–45 | — | — |
|  | SBO | — | −7 | 127 | — |

*SBO - soy bean oil;
CPD cyclopentadiene;
ISP - isoprene;
DMBD - dimethylbutadiene;
[H] - hydrogenated version of corresponding adduct.

TABLE VIII

| Sample | Iodine Value | Pour Point (° C.) | Unsaturation Content* | AOM (hrs) | Active** Methylenes |
|---|---|---|---|---|---|
| Typical Paraffin | 9.25 | −5 | | >169 | |
| Hydraulic Fluid SBO | 127.3 | −7 | 4.63 | 12.1 | 2.09 |
| Plant Hydro - F2 | 116.2 | −2 | 4.17 | 14 | 1.53 |
| Plant Hydro - F3 | 105.1 | 4 | | 18 | NA |
| Plant Hydro - F4 | 83.9 | 10 | 2.96 | | 0.38 |
| Plant Hydro - F5 | 73.8 | 14 | 2.62 | | 0.00 |
| Plant Hydro - F6 | 69.3 | 21 | 2.32 | | 0.00 |
| Plant Hydro - S8 | 29.7 | 43 | 0.93 | | 0.00 |
| SBO:DCPD adduct 93:7 | 127.2 | −12 | 4.33 | 81.1 | 1.94 |
| Adduct Hydro B (0.16) | 122 | −9 | 4.19 | | 1.93 |
| Adduct Hydro C (0.33) | | −9 | 4.09 | | 1.90 |
| Adduct Hydro D (1:00) | 76.3 | −5 | | | 1.53 |
| Adduct Hydro E (1:30) | 75 | 0 | 3.36 | | 0.86 |
| Adduct Hydro F (2:00) | | 2 | 3.17 | | 0.72 |
| Adduct Final (3:00) | 72.7 | 11 | 2.64 | 190.6 | 0.00 |

*Number of acylchain double bonds per molecule determined by NMR;
**Number of methylenes present in between the double bonds per molecule determined by NMR (i.e., number of doubly allylic methlene groups/molecule).

What is claimed is:

1. A process for modifying an unsaturated triacylglycerol oil comprising:
   reacting an unsaturated triacylglycerol oil having an Iodine Value of no more than about 150 and an active methylene content of no more than about 1.5 with an hydrocarbon diene and at a temperature of at least about 200° C. to form a cycloaddition product comprising triacylglycerol which have at least one unsaturated fatty acyl chain modified to include a cycloaddition adduct, wherein the cycloaddition product has a viscosity at 40° C. of no more than about 200 cP and an AOM value of at least about 50 hours; and
   at least partially hydrogenating the cycloaddition product in the presence of a hydrogenation catalyst to form a partially hydrogenated cycloaddition product having an Iodine Value of no more than about 150 and an active methylene content of no more than about 1.5.

2. The process of claim 1 wherein the at least partially hydrogenating step comprises at least partially hydrogenating the cycloaddition product to form a partially hydrogenated cycloaddition product having an Iodine Value reduced by at least about 10% with respect to that of the cycloaddition product.

3. The process of claim 1 wherein the at least partially hydrogenating step comprises at least partially hydrogenating the cycloaddition product to form a partially hydrogenated cycloaddition product having an active methylene content reduced by at least about 0.5 with respect to that of the cycloaddition product.

4. The process of claim 1 wherein the step of reacting comprises reacting the unsaturated triacylglycerol oil with the hydrocarbon diene at a temperature of no more than about 300° C.

5. The process of claim 1 wherein the reacting step comprises reacting the unsaturated triacylglycerol oil with hydrocarbon diene selected from the group consisting of cyclopentadiene, alkyl substituted cyclopentadienes, butadiene, alkyl substituted butadienes, and mixtures thereof.

6. The process of claim 1 wherein the reacting step comprises reacting the unsaturated triacylglycerol oil with hydrocarbon diene comprising cyclopentadiene.

7. The process of claim 6 wherein the reacting step comprises reacting the unsaturated triacylglycerol oil with hydrocarbon diene further comprising 1-methylcyclopentadiene and 2-methylcyclopentadiene.

8. The process of claim 1 wherein the reacting step comprises reacting the unsaturated triacylglycerol oil with sufficient hydrocarbon diene to form a cycloaddition product having an average cycloaddition content of at least about 0.25 adducts per triacylglycerol molecule.

9. The process of claim 1 wherein the unsaturated triacylglycerol oil has an Iodine Value of no more than about 110.

10. The process of claim 1 wherein the reacting step comprises reacting hydrocarbon diene with an unsaturated triacylglycerol oil selected from the group consisting of soybean oil, rapeseed oil, olive oil, sunflower oil, safflower oil, peanut oil, cottonseed oil, crambe oil, mustard oil, meadowfarm oil, herring oil, menhaden oil and mixtures thereof.

11. The process of claim 10 wherein the sunflower oil comprises a high oleic sunflower oil.

12. The process of claim 10 wherein the rapeseed oil comprises a high oleic canola oil.

13. The process of claim 1 wherein the reacting step comprises reacting an hydrocarbon diene with an unsaturated triacylglycerol oil comprising soybean oil.

14. The process of claim 1 wherein the step of reacting wherein the triacylglycerol is the diene, further including an isomerization step and includes heating the unsaturated triacylglycerol at a temperature between about 200° C. and about 300° C. in the presence of a conjugation catalyst.

15. The process of claim 14 wherein the step of reacting includes heating the unsaturated triacylglycerol at a temperature between about 200° C. and about 300° C. in the presence of about 0.001% to about 1.5% conjugation catalyst, by weight of the unsaturated triacylglycerol.

16. The process of claim 14 wherein the conjugation catalyst is selected from ruthenium, rhodium, nickel, nickel compounds, sulfur dioxide, iodine, hydriodic acid, iodine mono-chloride, iodine trichloride, iodine mono-bromine.

17. A modified unsaturated triacylglycerol oil comprising triacylglycerol which include at least one unsaturated fatty acyl chain modified to include an hydrogenated cycloaddition adduct; wherein said modified unsaturated triacylglycerol oil has a viscosity at 40° C. of no more than about 100 cP; an AOM value of at least about 50 hours; an Iodine Value of no more than about 150; and an active methylene content of no more than about 1.5.

18. The modified unsaturated triacylglycerol oil of claim 17 having an AOM value of at least about 100 hours.

19. The modified unsaturated triacylglycerol oil of claim 17 having an Iodine Value of no more than about 130.

20. The modified unsaturated triacylglycerol oil of claim 17 having an active methylene content of no more than about 1.5.

21. A method for producing a lubricant base stock comprising:

reacting an unsaturated triacylglycerol oil with an hydrocarbon diene at a temperature of at least about 200° C. to form a cycloaddition product comprising triacylglycerol that have an average cycloaddition content of at least about 0.25 adducts per triacylglycerol molecule; and at least partially hydrogenating the cycloaddition product in the presence of a hydrogenation catalyst to form a partially hydrogenated cycloaddition product having a viscosity at 40 C of no more than about 200 cP; an AOM value of at least about 50 hours; an Iodine Value of no more than about 150 and an active methylene content of no more than about 1.5.

22. The method of claim 21 wherein the unsaturated triacylglycerol oil has an Iodine Value of no more than about 140.

23. The method of claim 21 wherein the hydrogenated cycloaddition product has an Iodine Value reduced by at least about 10 Iodine Value units with respect to that of the cycloaddition product.

24. The method of claim 21 further comprising blending the hydrogenated cycloaddition product with a petroleum based lubricant base stock.

25. A lubricant composition comprising a base stock of unsaturated triacylglycerol modified by reacting the unsaturated triacylglycerol with a cyclic hydrocarbon diene in the presence of a conjugation catalyst and at a temperature at least about 200° C. to have an average cycloaddition content of at least about 0.25 adducts per triacylglycerol molecule, wherein the lubricant has a viscosity at 40° C. of no more than about 100 cP; an AOM value of at least about 50 hours; an Iodine Value of no more than about 150; and an active methylene content of no more than about 1.5.

26. The process of claim 1 wherein the hydrogenation catalyst is a heterogeneous noble or transition metal hydrogenation catalyst.

27. The process of claim 1 wherein the hydrocarbon diene comprises a cyclic hydrocarbon diene.

28. A process for producing a lubricant base stock comprising:

reacting an unsaturated triacylglycerol oil with an hydrocarbon diene at a temperature of at least about 200° C. to form a cycloaddition product comprising triacylglycerol which have at least one unsaturated fatty acyl chain modified to include a cycloaddition adduct wherein the cycloaddition product has a viscosity at 40° C. of no more than about 200 cP and an AOM value of at least about 50 hours; and partially hydrogenating the cycloaddition product in the presence of a hydrogenation catalyst to produce a partially hydrogenated cycloaddition product; wherein the unsaturated triacylglycerol oil has an Iodine Value of about 50 to about 150 and an active methylene content of no more than about 1.5.

29. The process of claim 28 wherein the partially hydrogenated cycloaddition product has an Iodine Value at least about 10% lower than that of the cycloaddition product.

30. The process of claim 29 further comprising fractionating the partially hydrogenated cycloaddition product to produce a fractionated cycloaddition product having an Iodine Value at least about 10% higher than that of the partially hydrogenated cycloaddition product.

31. A lubricant base oil stock formed by a process comprising:

reacting an hydrocarbon diene with an unsaturated triacylglycerol to form a cycloaddition product comprising a triacylglycerol having at least one unsaturated fatty acyl chain modified to include a cycloaddition adduct, and at least partially hydrogenating the cycloaddition product to form a partially hydrogenated cycloaddition product, wherein the partially hydrogenated cycloaddition product has a viscosity at 40° C. of no more than about 200 cP; an AOM value of at least about 50 hours; an Iodine Value of no more than about 150; and an active methylene content of no more than about 1.5.

32. The process of claim 27 wherein the cycloaddition product comprises a bulky bicyclic ring attached onto the acycl ring chain of the triacylglycerides.

33. A method of reducing friction between moving parts comprising applying a lubricant composition to at least one of said moving parts, wherein the lubricant composition comprises a base stock of at least one unsaturated triacylglycerol oil modified by reacting the unsaturated triacylglycerol with a cyclic hydrocarbon diene at a temperature of at least about 200° C. to provide a cycloaddition product having an average cycloaddition content of at least about 0.25 adducts per triacylglycerol molecule, wherein the lubricant has a viscosity at 40° C. of no more than about 100 cP; an AOM value of at least about 50 hours; an Iodine Value of no more than about 110; and an active methylene content of no more than about 1.5.

34. The process of claim 1 wherein the hydrogenation catalyst is selected from palladium, platinum, nickel, copper-chromium.

35. The process of claim 28 wherein the partially hydrogenated cycloaddition product has an active methylene content at least about 10% lower than that of the unsaturated triacylglycerol oil.

* * * * *